(12) United States Patent
Fischer et al.

(10) Patent No.: US 12,727,902 B2
(45) Date of Patent: Sep. 8, 2026

(54) CUTTING MECHANISM WITH CONSTANT-FORCE RETRACTION AND BAILOUT

(71) Applicant: CILAG GMBH INTERNATIONAL, Zug (CH)

(72) Inventors: Austin Michael Fischer, Cincinnati, OH (US); Christopher William Birri, West Chester, OH (US); Reed Arenburg, Cincinnati, OH (US)

(73) Assignee: Cilag GmbH International, Zug (CH)

(*) Notice: Subject to any disclaimer, the term of this patent is extended or adjusted under 35 U.S.C. 154(b) by 377 days.

(21) Appl. No.: 18/356,140

(22) Filed: Jul. 20, 2023

(65) Prior Publication Data

US 2025/0025195 A1 Jan. 23, 2025

(51) Int. Cl.

| | |
|---|---|
| ***A61B 17/295*** | (2006.01) |
| ***A61B 17/29*** | (2006.01) |
| ***A61B 34/30*** | (2016.01) |

(52) U.S. Cl.

CPC .... *A61B 17/295* (2013.01); *A61B 2017/2903* (2013.01); *A61B 34/30* (2016.02); *A61B 2034/305* (2016.02)

(58) Field of Classification Search

CPC . A61B 34/71; A61B 34/30; A61B 2017/2903; A61B 17/295

See application file for complete search history.

(56) References Cited

U.S. PATENT DOCUMENTS

| | | | | |
|---|---|---|---|---|
| 2017/0252096 | A1 * | 9/2017 | Felder | A61B 18/1445 |
| 2019/0125467 | A1 * | 5/2019 | Evans | B25J 9/1689 |

* cited by examiner

*Primary Examiner* — Mohamed G Gabr
*Assistant Examiner* — Khoa Tan Le
(74) *Attorney, Agent, or Firm* — Vorys, Sater, Seymour and Pease LLP

(57) ABSTRACT

A surgical tool includes a drive housing, a drive input rotatably mounted to a bottom of the drive housing, a capstan assembly arranged within the drive housing and operatively coupled to the drive input such that rotation of the drive input correspondingly actuates the capstan assembly, a longitudinally driven gear engageable with the drive gear, a drive rod coupled to the longitudinally driven gear and extending from the drive housing to an end effector of the surgical instrument and at least one biasing member mounted to the drive housing and operatively coupled to at least one of the capstan assembly and the longitudinally driven gear. The biasing member biases the longitudinally driven gear toward a proximal position with a constant force.

16 Claims, 11 Drawing Sheets

208
508
506a
508
506c
506e
506f
502
506d
504
508
506b
202
A1

202
602c
606c
608c
408c
604e
602e
408d
608e
606e
208
604c
614
606a
602a
604a
610
408a
604d
610
416
604b
612
602b
610
606b
602d
608d
606d
408b
610
602f
604f
608f
606f

CUTTING MECHANISM WITH CONSTANT-FORCE RETRACTION AND BAILOUT

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

Some end effectors include a cutting instrument or "knife" operable to traverse a guide track to sever tissue. Some end effectors are further operable to deploy staples or sutures as the knife is fired along the guide track. As the end effector is articulated, the geometry of the guide track changes, and thus, the position of the knife must be controlled to compensate for the changing geometry. Robotic systems may employ control algorithms to effectively control the position of the knife, but in the event of a system failure (loss of power, etc.), the knife should be retracted to a safe position. If left exposed, the knife may present hazards when cleaning and preparing the surgical instrument for future surgical operations.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to retracting drive cables and other mechanisms, which operate the surgical tool.

Embodiments discussed herein describe a surgical tool that includes a drive housing, a drive input rotatably mounted to a bottom of the drive housing, and a capstan assembly arranged within the drive housing and operatively coupled to the drive input such that rotation of the drive input correspondingly actuates the capstan assembly. A retraction mechanism is operably coupled to the capstan assembly to bias the capstan assembly to a "zero" or "home" position. The retraction mechanism may passively adjust a position of a knife driven by the capstan assembly, and may return the knife to a retracted position during bailout operations.

Embodiments of the retraction mechanisms included herein also describe constant-force springs that apply a constant load on the knife. Compared to extension spring or torque springs, the constant-force springs allow for higher maximum forces to be applied to the knife in a fully extended position. The constant-force spring may be coupled to a longitudinally driven member to remove backlash from gearing interfaces, which may improve accuracy when positioning the knife. Multiple constant-force springs may be provided in stacked or spaced configurations, which may facilitate assembly and adjustment of the force provide by the retraction mechanisms.

Figure 1:
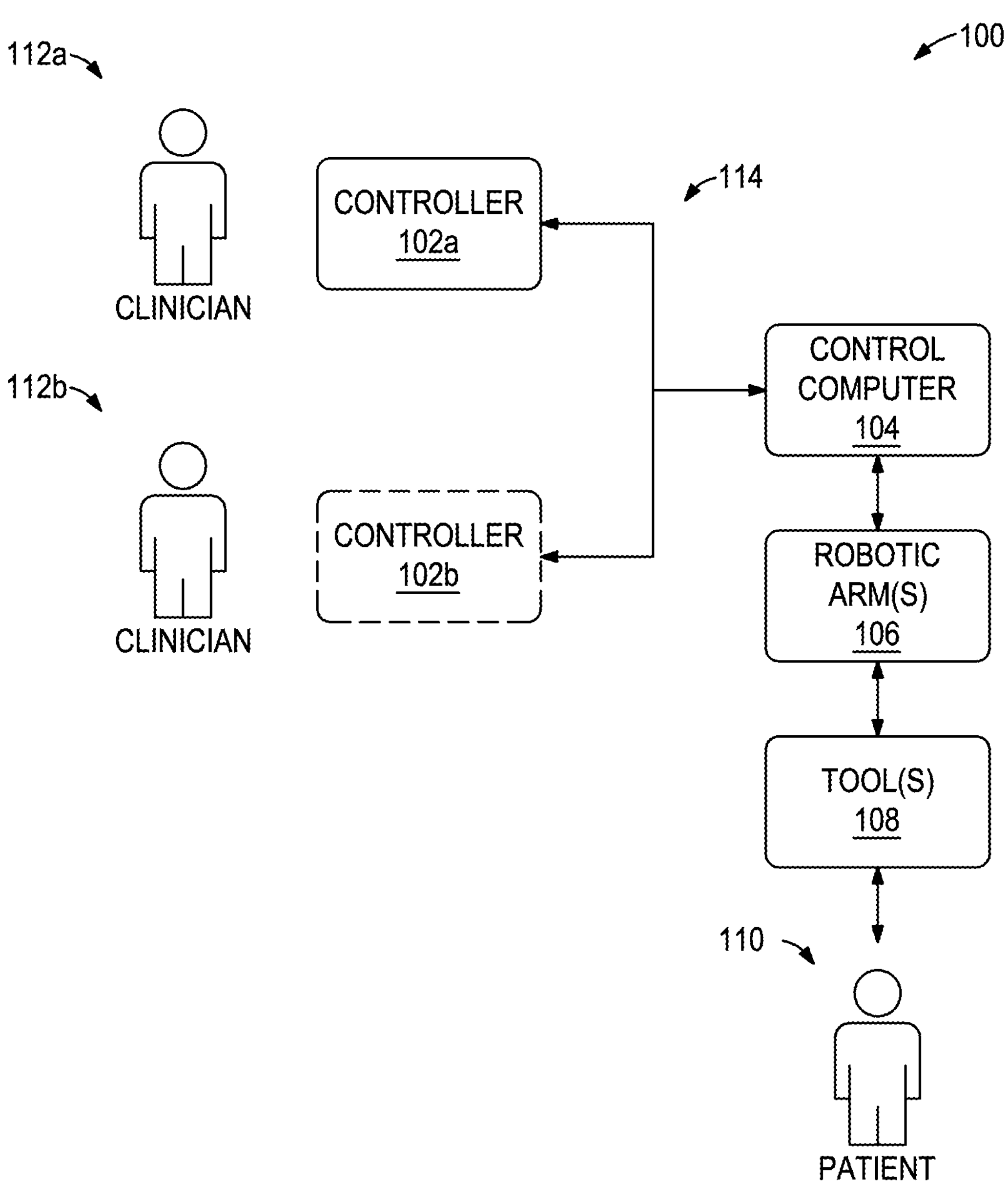
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between the clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
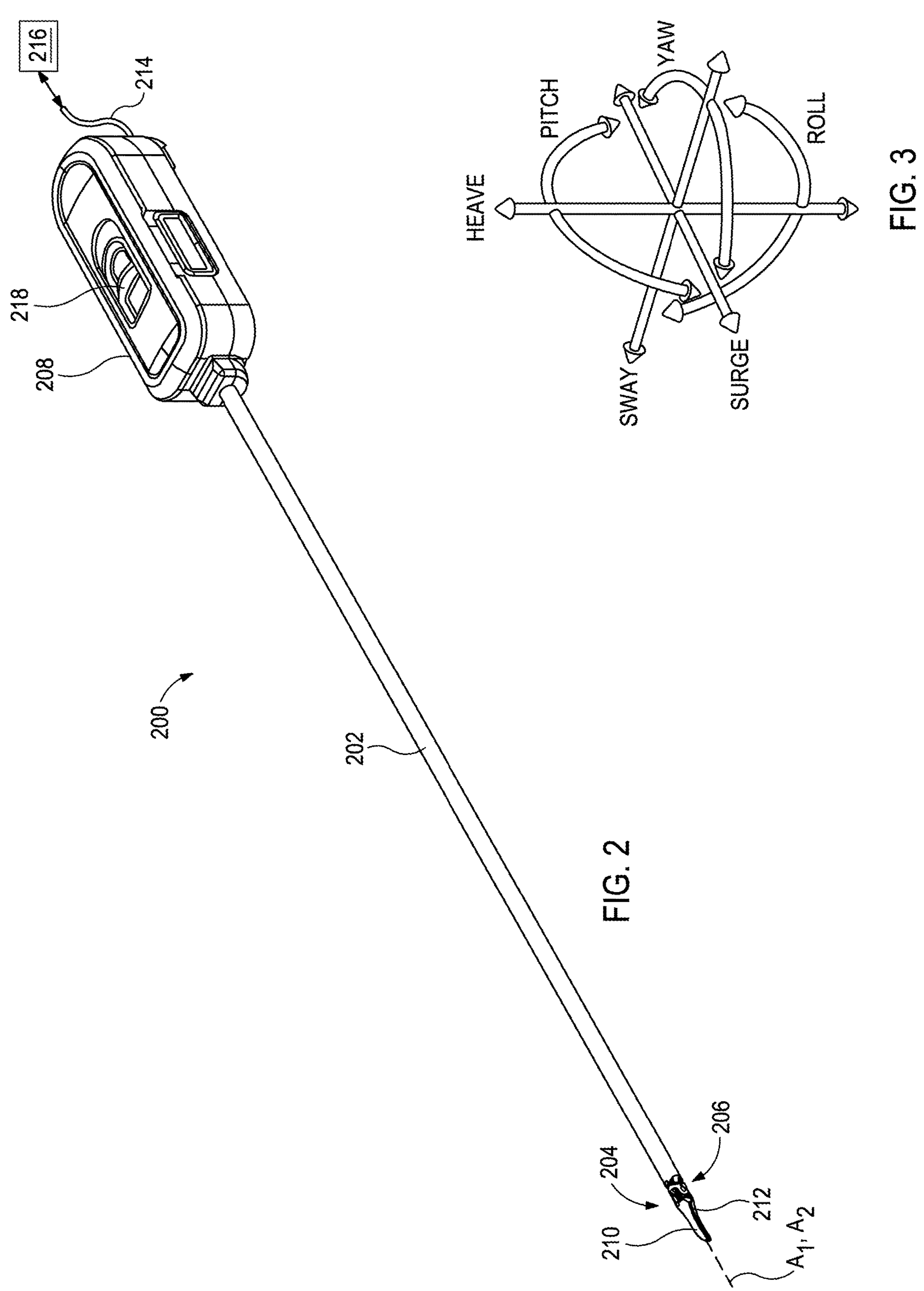
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can exhibit a variety of sizes, shapes, and configurations. In the illustrated embodiment, the end effector 204 comprises a combination tissue grasper and vessel sealer that include opposing first (upper) and second (lower) jaws 210, 212 configured to move (articulate) between open and closed positions. As will be appreciated, however, the opposing jaws 210, 212 may alternatively form part of other types of end effectors such as, but not limited to, a surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot to articulate the end effector 204 between the open and closed positions.

FIG. 3 illustrates the potential degrees of freedom in which the wrist 206 may be able to articulate (pivot) and thereby move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Moving (actuating) one or more of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the housing 208. In other embodiments, the power cable 214 may be omitted and electrical power may be supplied to the surgical tool 200 via an internal power source, such as one or more batteries, capacitors, or fuel cells. In such embodiments, the surgical tool 200 may alternatively be characterized and otherwise referred to as an "electrosurgical instrument" capable of providing electrical energy to the end effector 204.

The power cable 214 may place the surgical tool 200 in electrical communication with a generator 216 that supplies energy, such as electrical energy (e.g., radio frequency energy), ultrasonic energy, microwave energy, heat energy, or any combination thereof, to the surgical tool 200 and, more particularly, to the end effector 204. Accordingly, the generator 216 may comprise a radio frequency (RF) source, an ultrasonic source, a direct current source, and/or any other suitable type of electrical energy source that may be activated independently or simultaneously.

In applications where the surgical tool 200 is configured for bipolar operation, the power cable 214 will include a supply conductor and a return conductor. Current can be supplied from the generator 216 to an active (or source) electrode located at the end effector 204 via the supply conductor, and current can flow back to the generator 216 via a return electrode located at the end effector 204 via the return conductor. In the case of a bipolar grasper with opposing jaws, for example, the jaws serve as the electrodes where the proximal end of the jaws are isolated from one another and the inner surface of the jaws (i.e., the area of the jaws that grasp tissue) apply the current in a controlled path through the tissue. In applications where the surgical tool 200 is configured for monopolar operation, the generator 216 transmits current through a supply conductor to an active electrode located at the end effector 204, and current is returned (dissipated) through a return electrode (e.g., a grounding pad) separately coupled to a patient's body.

The surgical tool 200 may further include a manual release switch 218 that may be manually actuated by a user (e.g., a surgeon) to override the cable driven system and thereby manually articulate or operate the end effector 204. The release switch 218 is movably positioned on the drive housing 208, and a user is able to manually move (slide) the release switch 218 from a disengaged position, as shown, to an engaged position. In the disengaged position, the surgical tool 200 is able to operate as normal. As the release switch 218 moves to the engaged position, however, various internal component parts of the drive housing 208 are simultaneously moved, thereby resulting in the jaws 210, 212 opening, which might prove beneficial for a variety of reasons. In some applications, for example, the release switch 218 may be moved in the event of an electrical disruption that renders the surgical tool 200 inoperable. In such applications, the user would be able to manually open the jaws 210, 212 and thereby release any grasped tissue and remove the surgical tool 200. In other applications, the release switch 218 may be actuated (enabled) to open the jaws 210, 212 in preparation for cleaning and/or sterilization of the surgical tool 200.

Figure 4A:
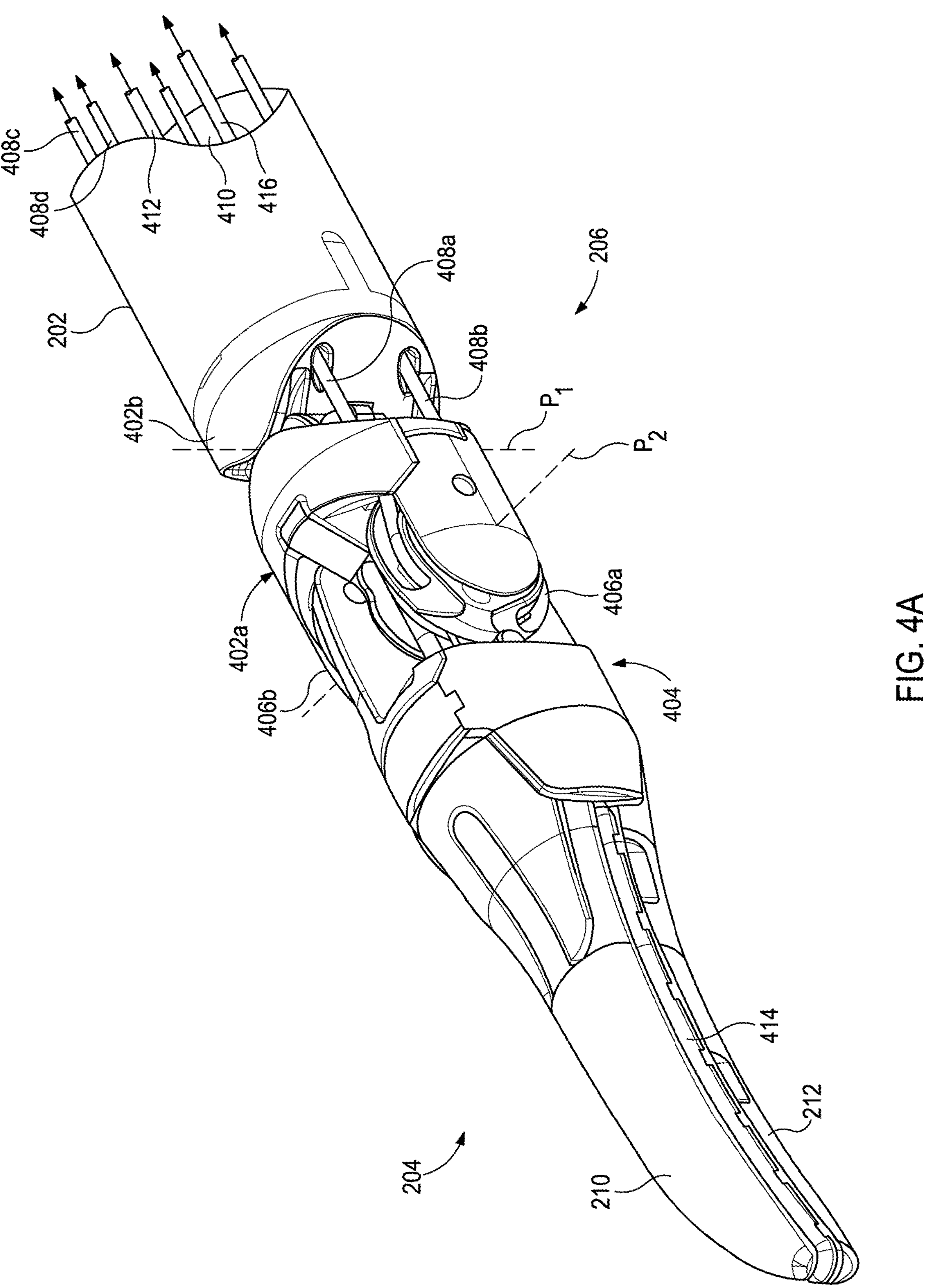
FIG. 4A is an enlarged isometric view of the distal end of the surgical tool of FIG. 2.

FIG. 4A is an enlarged isometric view of the distal end of the surgical tool 200. More specifically, FIG. 4A depicts an enlarged view of the end effector 204 and the wrist 206, with the jaws 210, 212 of the end effector 204 in the closed position. The wrist 206 operatively couples the end effector 204 to the shaft 202. In some embodiments, however, a shaft adapter may be directly coupled to the wrist 206 and otherwise interpose the shaft 202 and the wrist 206. Accordingly, the wrist 206 may be operatively coupled to the shaft 202 either through a direct coupling engagement where the wrist 206 is directly coupled to the distal end of the shaft 202, or an indirect coupling engagement where a shaft adapter interposes the wrist 206 and the distal end of the shaft 202. As used herein, the term "operatively couple" refers to a direct or indirect coupling engagement between two components.

To operatively couple the end effector 204 to the shaft 202, the wrist 206 includes a first or "distal" clevis **402*a* and a second or "proximal" clevis 402*b*. The clevises 402*a,b* are alternatively referred to as "articulation joints" of the wrist 206 and extend from the shaft 202 (or alternatively a shaft adapter). The clevises 402*a,b* are operatively coupled to facilitate articulation of the wrist 206 relative to the shaft 202. As illustrated, the wrist 206 also includes a linkage 404 arranged distal to the distal clevis 402*a* and operatively mounted to the jaws 210, 212**.

The proximal end of the distal clevis **402*a* may be rotatably mounted or pivotably coupled to the proximal clevis 402*b* at a first pivot axis $P_1$ of the wrist 206. In some embodiments, an axle may extend through the first pivot axis $P_1$ and the distal and proximal clevises 402*a,b* may be rotatably coupled via the axle. In other embodiments, however, such as is depicted in FIG. 4A, the distal and proximal clevises 402***a,b* may be engaged in rolling contact, such as via an intermeshed gear relationship that allows the clevises 402*a,b* to rotate relative to each other similar to a rolling joint.

First and second pulleys 406*a* and 406*b* may be rotatably mounted to the distal end of the distal clevis 402*a* at a second pivot axis $P_2$ of the wrist 206. The linkage 404 may be arranged distal to the second pivot axis $P_2$ and operatively mounted to the jaws 210, 212. The first pivot axis $P_1$ is substantially perpendicular (orthogonal) to the longitudinal axis $A_1$ of the shaft 202, and the second pivot axis $P_2$ is substantially perpendicular (orthogonal) to both the longitudinal axis $A_1$ and the first pivot axis $P_1$. Movement of the end effector 204 about the first pivot axis $P_1$ provides "yaw" articulation of the wrist 206, and movement about the second pivot axis $P_2$ provides "pitch" articulation of the wrist 206.

A plurality of drive cables, shown as drive cables 408*a*, 408*b*, 408*c*, and 408*d*, extend longitudinally within a lumen 410 defined by the shaft 202 (or a shaft adaptor) and extend at least partially through the wrist 206. The drive cables 408*a-d* may form part of the cable driven motion system housed within the drive housing 208 (FIG. 2), and may comprise cables, bands, lines, cords, wires, woven wires, ropes, strings, twisted strings, elongate members, belts, shafts, flexible shafts, drive rods, or any combination thereof. The drive cables 408*a-d* can be made from a variety of materials including, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof. While four drive cables 408*a-d* are depicted in FIG. 4A, more or less than four may be employed, without departing from the scope of the disclosure.

The drive cables 408*a-d* extend proximally from the end effector 204 and the wrist 206 toward the drive housing 208 (FIG. 2) where they are operatively coupled to various actuation mechanisms or devices that facilitate longitudinal movement (translation) of the drive cables 408*a-d* within the lumen 410. Selective actuation of the drive cables 408*a-d* applies tension (i.e., pull force) to the given drive cable 408*a-d* in the proximal direction, which urges the given drive cable 408*a-d* to translate longitudinally within the lumen 410.

In the illustrated embodiment, the drive cables 408*a-d* each extend longitudinally through the proximal clevis 402*b*. The distal end of each drive cable 408*a-d* terminates at the first or second pulleys 406*a,b*, thus operatively coupling each drive cable 408*a-d* to the end effector 204. In some embodiments, the distal ends of the first and second drive cables 408*a,b* may be coupled to each other and terminate at the first pulley 406*a*, and the distal ends of the third and fourth drive cables 408*c,d* may be coupled to each other and terminate at the second pulley 406*b*. In at least one embodiment, the distal ends of the first and second drive cables 408*a,b* and the distal ends of the third and fourth drive cables 408*c,d* may each be coupled together at corresponding ball crimps (not shown) mounted to the first and second pulleys 406*a,b*, respectively.

In at least one embodiment, the drive cables 408*a-d* may operate "antagonistically". More specifically, when the first drive cable 408*a* is actuated (moved), the second drive cable 408*b* naturally follows as coupled to the first drive cable 408*a*, and when the third drive cable 408*c* is actuated, the fourth drive cable 408*d* naturally follows as coupled to the third drive cable 408*c*, and vice versa. Antagonistic operation of the drive cables 408*a-d* can open or close the jaws 210, 212. More specifically, selective actuation of the drive cables 408*a-d* in other known configurations or coordination will cause the jaws 210, 212 to open or close. Antagonistic operation of the drive cables 408*a-d* can further cause the end effector 204 to articulate at the wrist 206. More specifically, selective actuation of the drive cables 408*a-d* in known configurations or coordination can cause the end effector 204 to articulate about one or both of the pivot axes $P_1$, $P_2$, thus facilitating articulation of the end effector 204 in both pitch and yaw directions, either individually or simultaneously. Antagonistic operation of the drive cables 408*a-d* advantageously reduces the number of cables required to provide full wrist 206 motion, and also helps eliminate slack in the drive cables 408*a-d*, which results in more precise motion of the end effector 204.

In the illustrated embodiment, the end effector 204 is able to articulate (move) in pitch about the second or "pitch" pivot axis $P_2$, which is located near the distal end of the wrist 206. Thus, the jaws 210, 212 open and close in the direction of pitch. In other embodiments, however, the wrist 206 may alternatively be configured such that the second pivot axis $P_2$ facilitates yaw articulation of the jaws 210, 212, without departing from the scope of the disclosure.

In some embodiments, an electrical conductor 412 may also extend longitudinally within the lumen 410, through the wrist 206, and terminate at an electrode 414 to supply electrical energy to the end effector 204. In some embodiments, the electrical conductor 412 may comprise a wire, but may alternatively comprise a rigid or semi-rigid shaft, rod, or strip (ribbon) made of a conductive material. The electrical conductor 412 may be entirely or partially covered with an insulative covering (overmold) made of a non-conductive material. Using the electrical conductor 412 and the electrode 414, the end effector 204 may be configured for monopolar or bipolar RF operation.

In the illustrated embodiment, the end effector 204 comprises a combination tissue grasper and vessel sealer that includes a knife 420 (FIG. 4B), alternately referred to as a "cutting element" or "blade." The knife is aligned with and configured to traverse a guide track 422 (FIG. 4B) defined longitudinally in one or both of the upper and lower jaws 210, 212. The knife 420 may be operatively coupled to the distal end of a drive rod 416 that extends longitudinally within the lumen 410 and passes through the wrist 206. Longitudinal movement (translation) of the drive rod 416 correspondingly moves the knife 420 within the guide track(s) 422. Similar to the drive cables 408*a-d*, the drive rod 416 may form part of the actuation systems housed within the drive housing 208 (FIG. 2). Selective actuation of a corresponding drive input will cause the drive rod 416 to move distally or proximally within the lumen 410, and correspondingly move the knife 420 in the same longitudinal direction.

Figure 4B:
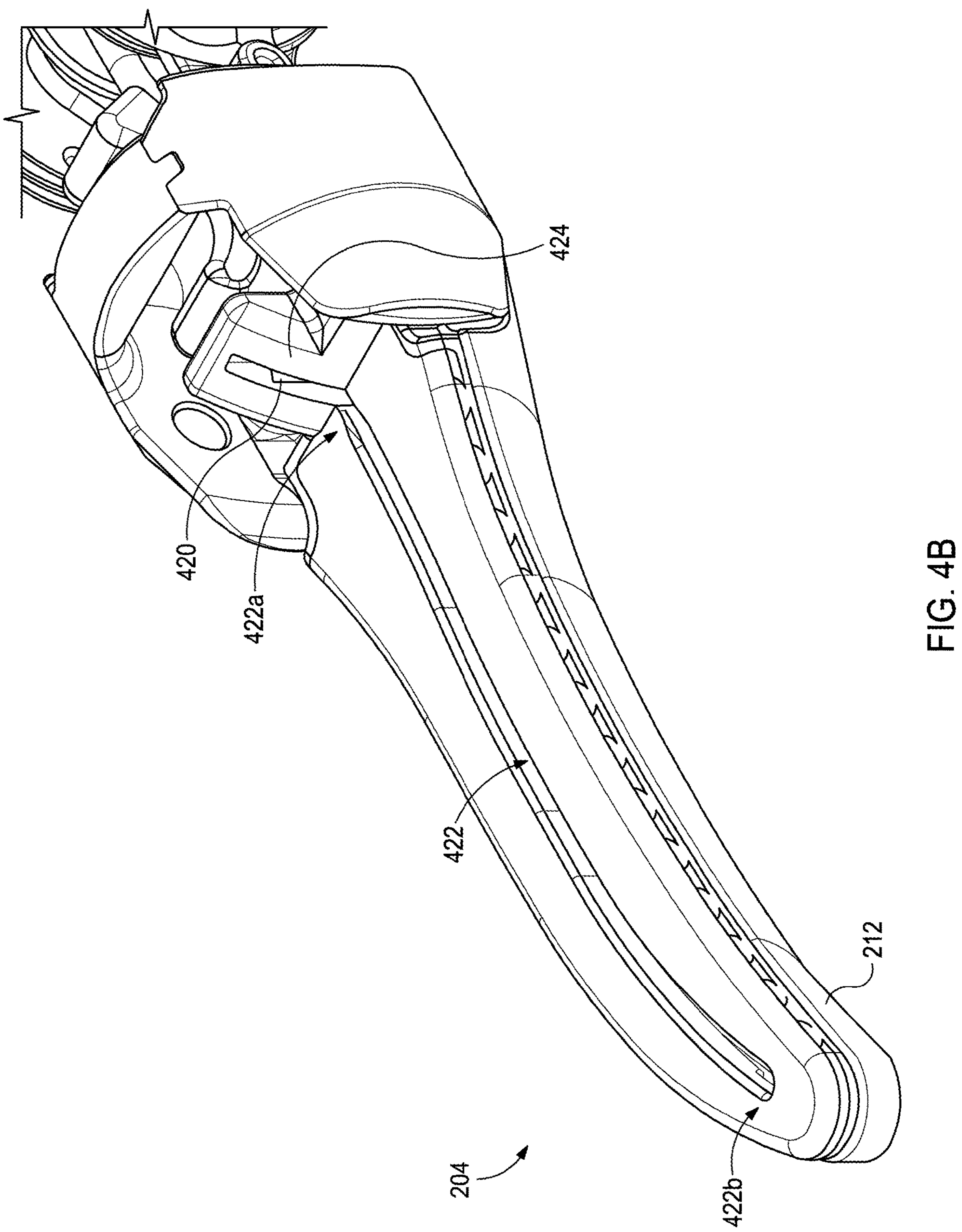
FIG. 4B is a partial isometric view of the distal end of the surgical tool of FIG. 2 with a jaw removed.

FIG. 4B is a partial isometric view of the distal end of the surgical tool 200 with the first jaw 210 (FIG. 4A) removed. With the first jaw 210 removed, the guide track 422 defined in the second jaw 212 is visible extending from a proximal end 422*a* to a distal end 422*b*. In some embodiments, the first jaw 210 may include a similar or complimentary guide track (not shown) in opposition to the guide track 422 when the first and second jaws 210, 212 are closed. The knife 420 is illustrated in a "zero" or "home" position wherein the knife 420 is disposed within a knife housing 424 adjacent the proximal end 422*a* of the guide track 422. The knife housing 424 may be constructed of the insulative covering (overmold) described above, or may be constructed as a separate component. When the knife 420 is disposed within the knife housing 424, the end effector 204 may be safely handled for cleaning or maintenance. In operation, the knife 420 may be selectively moved distally out of the knife housing 424 along the guide track 422 by longitudinally moving the drive rod 416 as described above.

Figure 5:
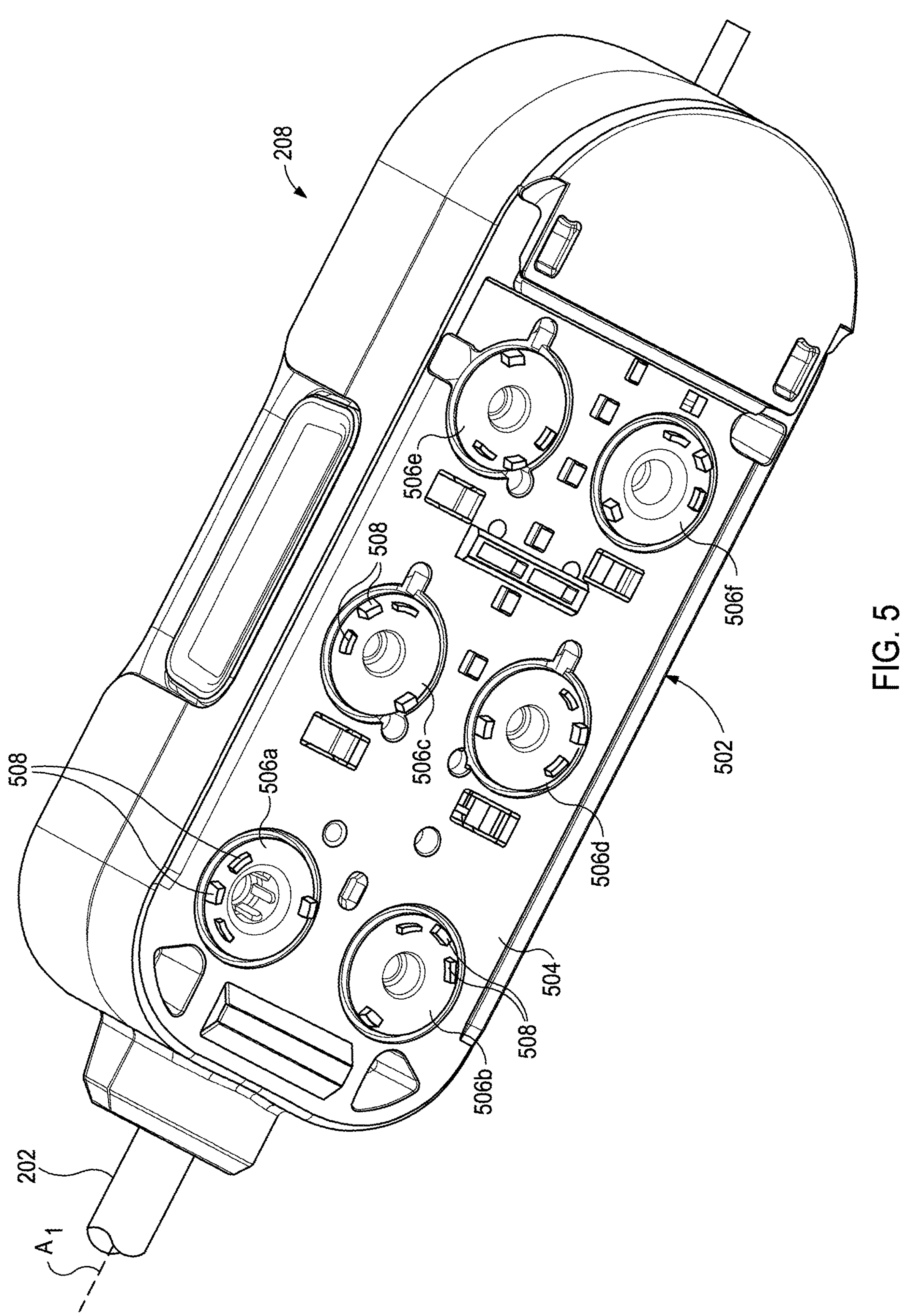
FIG. 5 is a bottom view of the drive housing of FIG. 2, according to one or more embodiments.

FIG. 5 is a bottom view of the drive housing 208, according to one or more embodiments. As illustrated, the drive housing 208 may include a tool mounting portion 502 used to operatively couple the drive housing 208 to a tool driver of a robotic manipulator. The tool mounting portion 502 may releasably couple the drive housing 208 to a tool driver in a variety of ways, such as by clamping thereto, clipping thereto, or slidably mating therewith. In some embodiments, the tool mounting portion 502 may include an array of electrical connecting pins, which may be coupled to an electrical connection on the mounting surface of the tool driver. While the tool mounting portion 502 is described herein with reference to mechanical, electrical, and magnetic coupling elements, it should be understood that a wide variety of telemetry modalities might be used, including infrared, inductive coupling, or the like.

The tool mounting portion 502 includes and otherwise provides an interface 504 configured to mechanically, magnetically, and/or electrically couple the drive housing 208 to the tool driver. As illustrated, the interface 504 includes and supports a plurality of drive inputs, shown as drive inputs 506*a*, 506*b*, 506*c*, 506*d*, 506*e*, and 506*f*. Each drive input 506*a-f* comprises a rotatable disc configured to align with and couple to a corresponding actuator or "drive output" of a tool driver, such that rotation (actuation) of a given drive output drives (rotates) a corresponding one of the drive inputs 506*a-f*. Each drive input 506*a-f* may provide or define one or more surface features 508 configured to align with mating surface features provided on the corresponding drive output. The surface features 508 can include, for example, various protrusions and/or indentations that facilitate a mating engagement. In some embodiments, some or all of the drive inputs 506*a-f* may include one surface feature 508 that is positioned closer to an axis of rotation of the associated drive input 506*a-f* than the other surface feature(s) 508. This may help to ensure positive angular alignment of each drive input 506*a-f*.

In some embodiments, actuation of the first drive input 506*a* may be configured to control rotation of the shaft 202 about its longitudinal axis $A_1$. The shaft 202 may be rotated clockwise or counter-clockwise depending on the rotational actuation of the first drive input 506*a*. In some embodiments, actuation of the second, third, fourth, and fifth drive inputs 506*b-e* may be configured to operate movement (axial translation) of the drive cables 408*a-d* (FIG. 4A), which results in the actuation of the wrist 106 (FIG. 4A) and/or articulation (operation) of the end effector 204 (FIG. 4A). In some embodiments, actuation of the sixth drive input 506*f* may be configured to advance and retract the drive rod 416 (FIG. 4A), and thereby correspondingly advance or retract the knife 420 (FIG. 4B) at the end effector 204. Each of the drive inputs 506*a-f* may be actuated based on user inputs communicated to the tool driver coupled to the interface 504, and the user inputs may be received via a computer system incorporated into the robotic surgical system.

Figure 6:
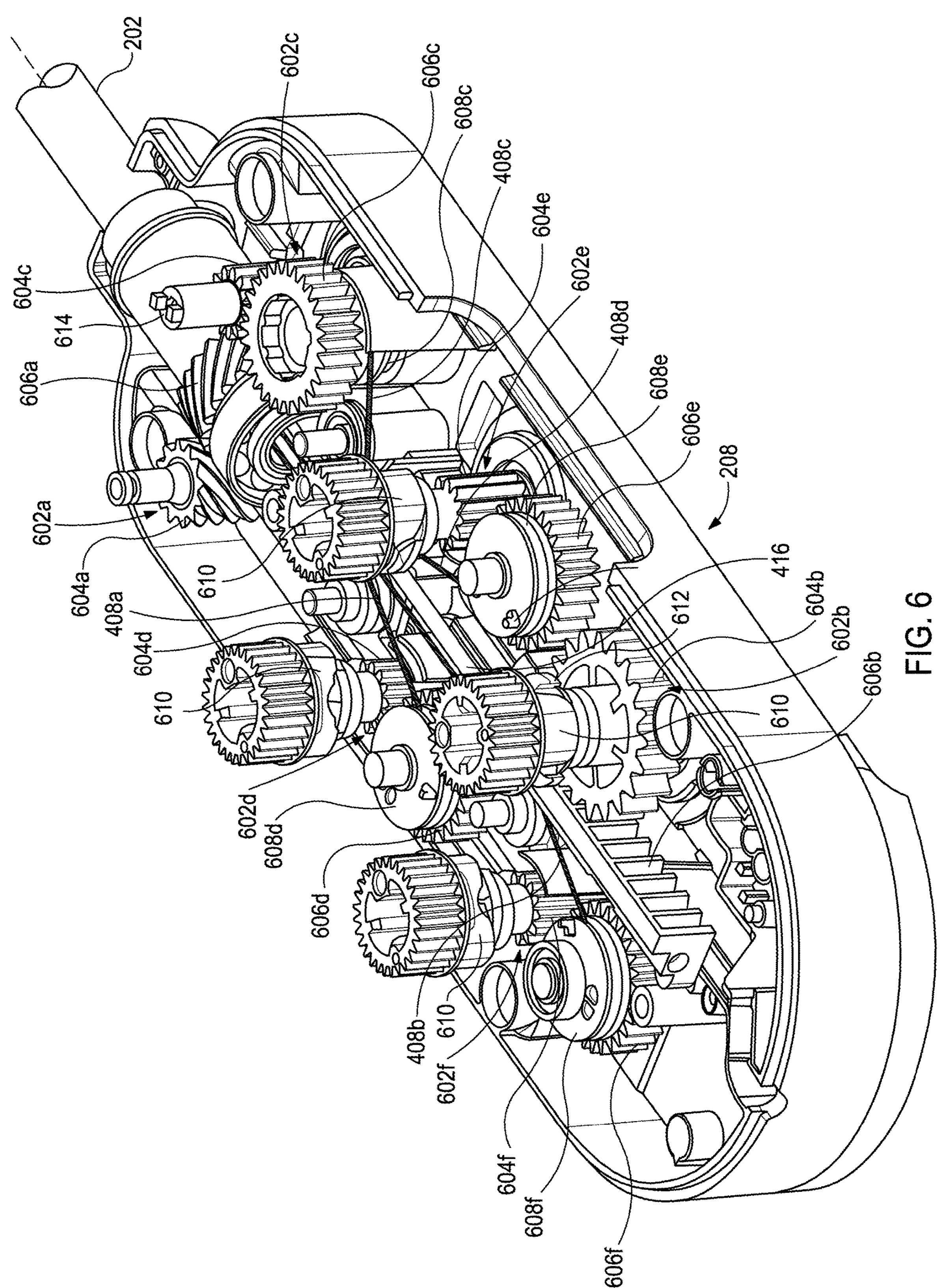
FIG. 6 is an exposed isometric view of the interior of the drive housing of FIG. 2, partially illustrating a plurality of capstan assemblies for driving a knife and other functions of the surgical tool, according to one or more embodiments.

FIG. 6 is an exposed isometric view of the interior of the drive housing 208, according to one or more embodiments. Several component parts that may be otherwise contained within the drive housing 208 are not shown in FIG. 6 to enable discussion of the depicted component parts. As illustrated, the drive housing 208 houses and otherwise contains a plurality of capstan assemblies operable to operate surgical tool 200 (FIG. 2). In particular, a first capstan assembly 602*a* is contained (housed) within the drive housing 208. As illustrated, the first capstan assembly 602*a* may include a drive gear 604*a*, which may be operatively coupled to or extend from the first drive input 506*a* (FIG. 5) such that actuation of the first drive input 506*a* results in rotation of the drive gear 604*a*. In the illustrated embodiment, the drive gear 604*a* comprises a worm gear, e.g., a crossed helical or screw gear, which may be configured to mesh and interact with a driven gear 606*a* secured within the drive housing 208 and operatively coupled to the shaft 202 such that rotation of the driven gear 606*a* correspondingly rotates the shaft 202. Accordingly, actuation of the first capstan assembly 602*a*, via actuation of the first drive input 506*a*, will drive the driven gear 606*a* and thereby control rotation of the elongate shaft 202 about the longitudinal axis $A_1$.

The drive housing 208 may further contain or house a second capstan assembly 602*b*, which may include a drive gear 604*b* operatively coupled to or extending from the sixth drive input 506*f* (FIG. 5) such that actuation of the sixth drive input 506*f* results in rotation of the drive gear 604*b*. The drive gear 604*b* is arranged to intermesh with a driven gear 606*b* positioned within the drive housing 208. In the illustrated embodiment, the driven gear 606*b* comprises a rack gear longitudinally translatable within the drive housing 208 as acted upon by the drive gear 604*b*. The drive rod 416 may be operatively coupled to the driven gear 606*b* and extend distally therefrom to the end effector 204 (FIGS. 2 and 4). Accordingly, actuation of the second capstan assembly 602*b*, via actuation of the sixth drive input 506*f*, will cause the driven gear 606*b* to longitudinally translate and correspondingly advance or retract the drive rod 416 and the knife 420 (FIG. 4B) coupled to the end of the drive rod 416 at the end effector 204.

The drive housing 208 further contains or houses third, fourth, fifth, and sixth capstan assemblies 602*c*, 602*d*, 602*e*, and 602*f*, alternately be referred to as "drive cable" capstan assemblies since they are operable to actuate the drive cables 408*a-d*, as described below. While four "drive cable" capstan assemblies 602*c-f* are depicted in FIG. 6, alternative embodiments may include more or less than four, depending on how many drive cables 408*a-d* are used.

In the illustrated embodiment, the third capstan assembly 602*c* is actuated through operation (rotation) of the second drive input 506*b* (FIG. 5), the fourth capstan assembly 602*d* is actuated through operation (rotation) of the third drive input 506*c* (FIG. 5), the fifth capstan assembly 602*e* is actuated through operation (rotation) of the fourth drive input 506*d* (FIG. 5), and the sixth capstan assembly 602*f* is actuated through operation (rotation) of the fifth drive input 506*e* (FIG. 5). As illustrated, each capstan assembly 602*c-f* includes a drive gear 604*c*, 604*d*, 604*e*, and 604*f* that is coupled to or extends from the corresponding drive input 506*b-e*, respectively, such that actuation (rotation) of the drive input 506*b-e* correspondingly rotates the associated drive gear 604*c-f*, respectively.

Moreover, each drive gear 604*c-f* is positioned to mesh and interact with a corresponding driven gear 606*c*, 606*d*, 606*e*, and 606*f* rotatably mounted within the drive housing 208. Each driven gear 606*c-f* includes or is otherwise coupled to a corresponding cable pulley 608*c*, 608*d*, 608*e*, and 608*f*, and each cable pulley 608*c-f* is configured to be operatively coupled to (e.g., has wrapped there around, at least partially) a corresponding one of the drive cables 408*a-d*. In the illustrated embodiment, the first drive cable 408*a* terminates at cable pulley 608*d* ultimately driven by actuation of the fourth capstan assembly 602*d*, the second drive cable 408*b* terminates at cable pulley 608*f* ultimately driven by actuation of the sixth capstan assembly 602*f*, the third drive cable 408*c* terminates at cable pulley 608*c* ultimately driven by actuation of the third capstan assembly 602*c*, and the fourth drive cable 408*d* terminates at cable pulley 608*e* ultimately driven by actuation of the fifth capstan assembly 602*e*.

Accordingly, actuation of the fourth capstan assembly 602*d* (via operation of the third drive input 506*c* of FIG. 5) will correspondingly control movement of the first drive cable 408*a*; actuation of the sixth capstan assembly 602*f* (via operation of the fifth drive input 506*e* of FIG. 5) will correspondingly control movement of the second drive cable 408*b*; actuation of the third capstan assembly 602*c* (via operation of the second drive input 506*b* of FIG. 5) will correspondingly control movement of the third drive cable 408*c*; and actuation of the fifth capstan assembly 602*e* (via operation of the fourth drive input 506*d* of FIG. 5) will correspondingly control movement of the fourth drive cable 408*d*.

Couplers for Retraction Mechanisms

Still referring to FIG. 6, each of the second, fourth, fifth and sixth capstan assemblies 602*b* and 602*d-f* may include a coupler 610 thereon for facilitating connection to a retraction mechanism (see FIG. 7) as described in greater detail below. The couplers 610 are operatively coupled to or extend from the respective third, fourth, fifth and sixth drive input 506*c-f* (FIG. 5) such that actuation of the respective drive input 506*c-f* results in rotation of the respective coupler along with the respective drive gear 604*d-f* and 604*b*. The couplers 610 include one or more hooks 612, which may be used to couple the retraction mechanisms to the capstan assemblies 602*b* and 602*d-f*, as described in greater detail below.

Although not shown in FIG. 6, an additional coupler 610 (FIG. 7) may also be secured to, or form part of, the third capstan assembly 602*c*. A castellated peg 614 is provided, operatively coupled to or extending from the third drive gear 604 such that actuation of the second drive input 506*b* results in rotation of the castellated peg 614 along with the third drive gear 604*c*. The castellated peg 614 may transmit torque to the additional coupler 610 coupled thereto such that the additional coupler 610 rotates along with the castellated peg 614, the third drive gear 604*c* and the second drive input 506*b*.

Figure 7:
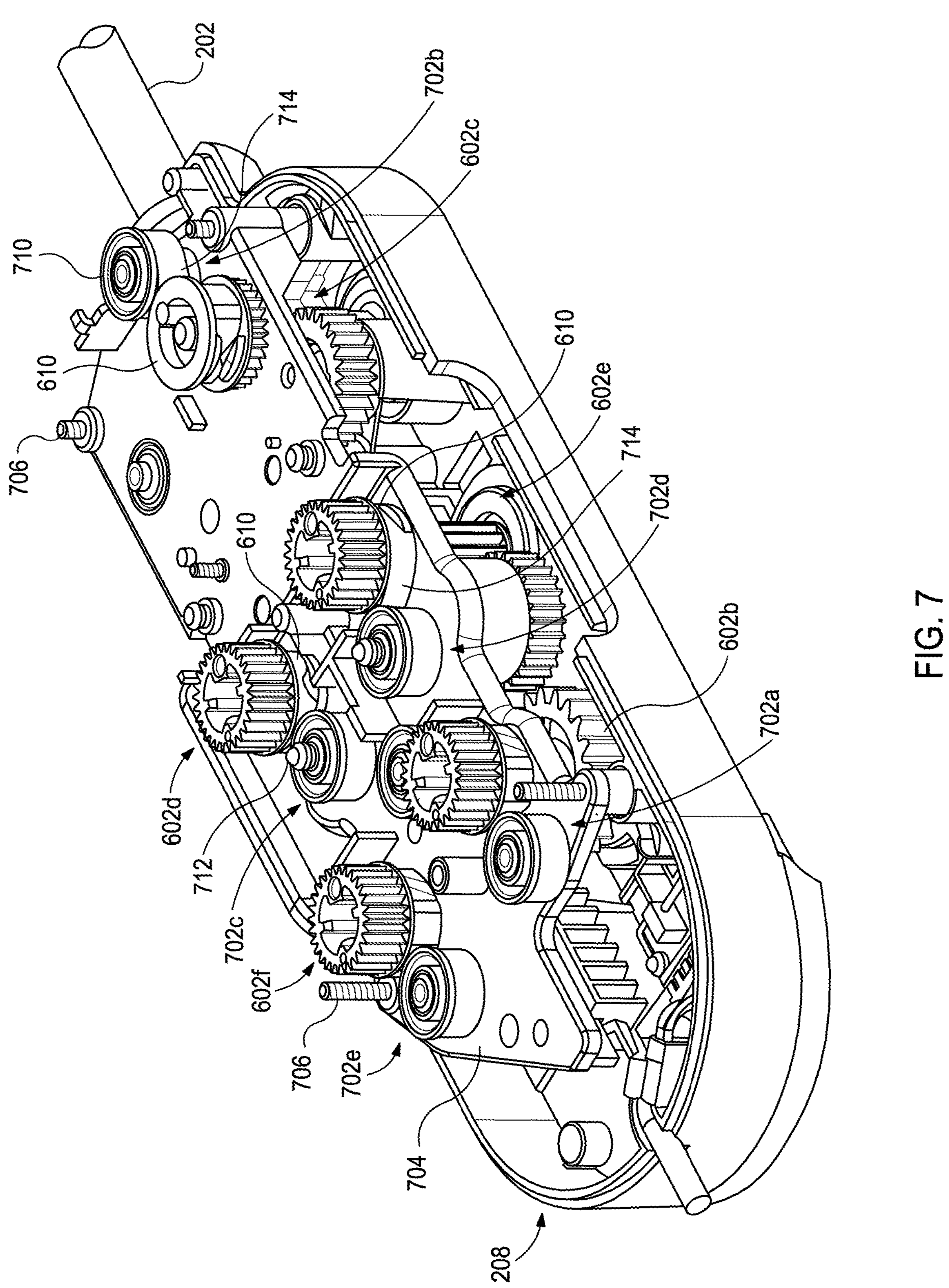
FIG. 7 is an exposed isometric view of the interior of the drive housing of FIG. 6, illustrating a retraction mechanism coupled to each of the capstan assemblies, according to one or more embodiments.

FIG. 7 an exposed isometric view of the interior of the drive housing 208, illustrating a constant-force or constant-torque retraction mechanism 702*a-e* (generally or collectively 702) coupled to each of the respective capstan assemblies 602*b-f*. The capstan assemblies 602*b-f* protrude through a chassis plate 704, which may be secured to the drive housing 208 in a fixed position with fasteners 706, ultrasonic welding, adhesives or other attachment mechanisms. A coupler 610 is secured to the capstan assembly 602*c*, and protrudes through the chassis plate 407 to facilitate coupling the third capstan assembly 602*c* to the retraction mechanism 702*b*. Although no retraction mechanism is illustrated in connection with the first capstan assembly 602*a*, which operates to rotate the shaft 202, it is contemplated herein that an additional retraction assembly may be operably coupled to the first capstan assembly 602*a* as well to bias the shaft 202 to a "zero" or "home" rotational position.

As illustrated, the retraction mechanisms 702 each include one or more spools 710 mounted to the chassis plate 704 with fasteners 712 or another attachment mechanism. The spools 710 may be attached to the chassis plate 704 in a fixed location with respect to the drive housing 208. In some embodiments the spools 710 may be fixedly attached to the chassis plate 704, or in some embodiments, the spools 710 may be permitted to rotate with respect to the chassis plate 704.

Each retraction mechanism 702 also includes a constant-force or constant torque spring 714 or other biasing member extending between and operably coupling the spools 710 to the couplers 610. The constant-force or constant torque springs 714 may be constructed generally as pre-stressed flat strips of spring material formed into virtually constant-radius coils around the spools 710. The springs 714 may be reverse wound onto the couplers 610 such that, when released, torque is applied to the respective capstan assembly 602*b-f* as the springs 714 return to their natural curvature. In some embodiments, the springs 714 may be provided without the spools 710. The springs 714 may be housed in a cavity (not shown), which may introduce friction and change the torque provided to the capstan assemblies 602*b-f*. In some embodiments, the springs 714 may be pre-stressed to provide near constant torque to the capstan assemblies 602*b-f*, or even negative torque in some instances. Negative gradients of up to 50% may be achieved.

The springs 714 may be constant force spring that applies a constant force to a rotational or linearly translating member, or a constant torque spring that applies a constant torque to a rotational member to provide a constant force on a driven member of the surgical tool 200. For example, as described in greater detail below, the spring 714 coupled to coupler 610 on the second capstan assembly 602*b* may apply a constant force or constant torque to the rotational drive gear 604*b* (FIG. 6) such that a constant force is imparted to the drive rod 416 driven by the second capstan assembly 602*b*. In other embodiments (see, e.g., FIG. 11), the springs 714 may apply a constant force to a linearly translating member, such as the longitudinally driven gear 1108, (FIG. 11) to impart a constant force to the drive rod 416 driven by the second capstan assembly 602*b*. Since the springs 714 operate to provide a constant force to the drive rod 416, the springs 714 (and other biasing mechanisms described herein) may be referred to as "constant-force springs" even if the springs provide a constant torque. Additionally, the springs 714 (and other biasing mechanisms described herein) may include a very low spring rate extension or compression spring where the spring provides a substantially constant force over the operating range of the drive rod 416.

In some embodiments, the constant-force springs 714 may comprise bands constructed of spring-steel, aluminum, titanium, a polymer, an elastomer, a fiber mesh, or any combination of the foregoing. The bands are illustrated as flat strips in FIG. 7, and other cross-sectional shapes such as circular, triangular, etc. are contemplated. In some embodiments, the bands are generally relaxed when fully coiled around the spools 710. When the bands are extended or deflected by a loading force, the internal stress in the bands resists the loading force at a nearly constant rate, which is in contrast to torsion springs or extension springs that progressively increase resistance rate with further deflection. An end of each of the constant-force springs 714 is secured to a respective coupler 610, e.g., by the hooks 612 (FIG. 6) such that rotation of the couplers 610 in a first direction winds the bands around the couplers 610 and thereby extends the bands from the spools 710. The constant-force springs 714 thus resist the rotation of the couplers 610 in the first direction. As described above, the couplers 610 are rotationally coupled to the capstan assemblies 602*b-f* that drive the end effector 204 (FIGS. 2 and 4) from a "zero" or "home" configuration, and thus the constant-force springs 714 resist the movement of the end effector 204 from the "zero" or "home" configuration.

Rotation of the couplers 610 in a second direction (opposite the first direction) unwinds the bands from the couplers 610 and allows the bands to be re-coiled onto the spools 710. The capstan assemblies 602*b-f* may be driven in the second direction by the tool driver as described above. Additionally, if the drive housing 208 is removed from the tool driver, the internal stress in the constant-force or constant-torque springs 714 will rotate the couplers 610 in the second direction and thereby return the end effector 204 (FIGS. 2 and 4) to the "zero" or "home" configuration.

Figure 8:
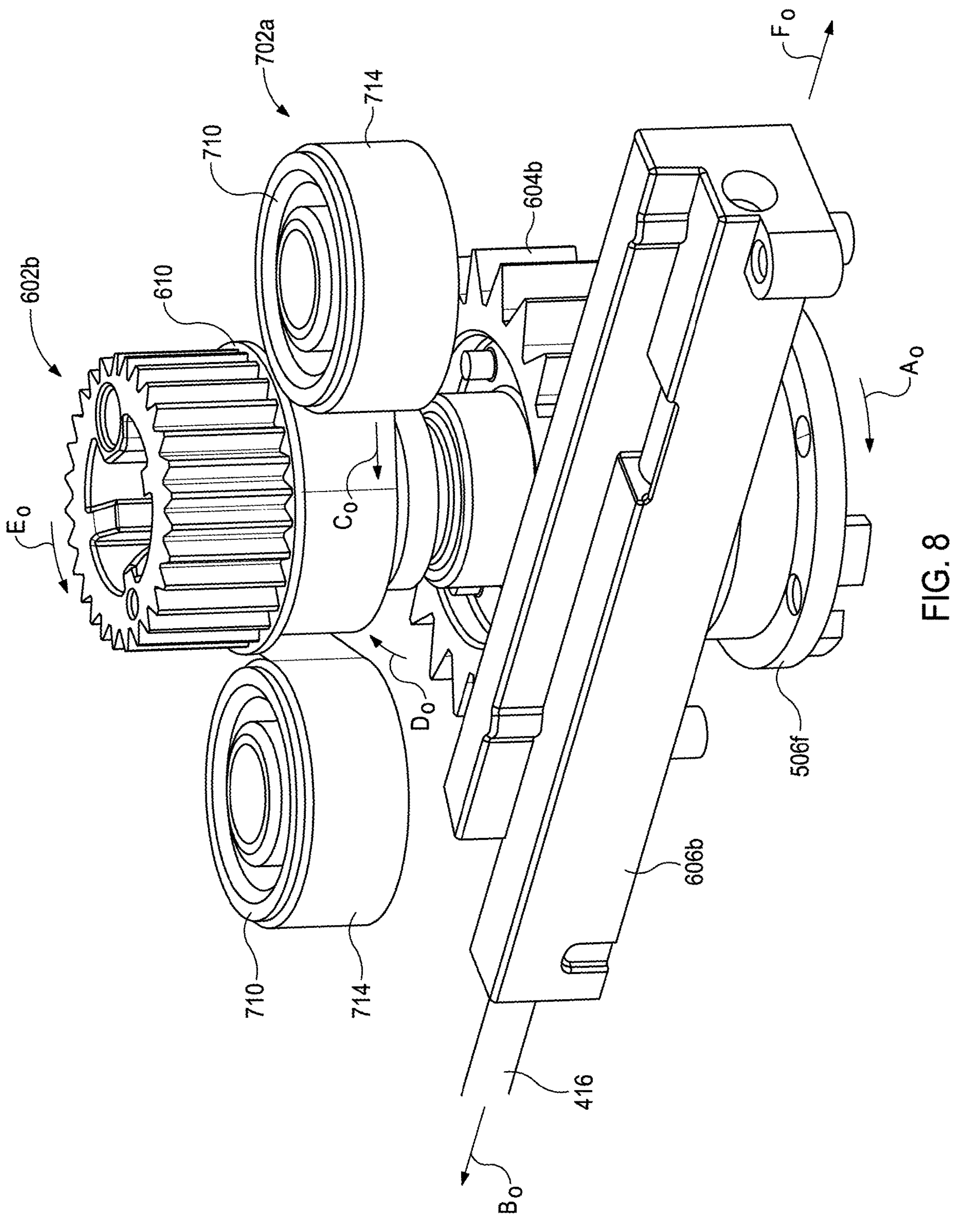
FIG. 8 is a perspective view of the capstan assembly of FIG. 6, which drives the knife, with the retraction mechanism of FIG. 7 coupled thereto.

FIG. 8 is a perspective view of the second capstan assembly 602*b*, which drives the knife 420 (FIG. 4B), and the retraction mechanism 702*a* operatively coupled to the second capstan assembly 602*b*. In the illustrated embodiment, the retraction mechanism 702*a* includes two constant-force springs 714 coupled to the coupler 610, but in other embodiments, more or fewer constant-force springs 714 may be provided without departing from the scope of the disclosure. The second capstan assembly 602*b* is illustrated in an initial rotational position where the driven gear 606*b* and the drive rod 416 are in a "zero" or "home" position where the knife 420 is retracted and not exposed. The two constant-force springs 714 bias the capstan assembly 602*b* to the initial rotational position. It should be appreciated that the "zero" or "home" position of the driven gear 606*b* illustrated is exemplary, and may not be the exact position of the driven gear 606*b* required to maintain the knife 420 in the retracted position given the state of the end effector 204 (FIG. 2). For example, if end effector 202 is in an articulated or unarticulated position, or if the jaws 210, 212 are opened or closed, the driven gear 606*b* may be moved to a slightly different position.

In operation, the sixth drive input 506*f* may be rotated, e.g., by a tool driver, in a first angular direction, as indicated by the arrows $A_0$. The drive gear 604*b* and the coupler 610 are thereby induced to also rotate in the direction of arrow $A_0$. Rotation of the drive gear 604*b* drives the driven gear 606*b* and the drive rod 416 in a distal direction, as indicated by arrow $B_0$. Rotation of the coupler 610 in the first angular direction $A_0$ draws the constant-force or constant torque springs 714 in the direction of arrows $C_0$ and $D_0$ around the coupler 610 as the constant-force springs 714 progressively unwind from their respective spools 710. The constant-force springs naturally 714 resist the rotation of the drive gear 604*b* and the distal advancement of the driven gear 606*b* and the drive rod 416 at a constant rate. Since the resistance of the constant-force springs 714 does not increase (or decrease) during actuation, the knife 420 may provide the same cutting force at the distal end 422*b* (FIG. 4B) of the guide track 422 as the knife 420 provides at the proximal end 422*a* of the guide track 422. This arrangement allows for a higher maximum knife output of the blade in the fully extended (distal-most) position than a system in which resistance to the distal motion of the knife 420 increases as the knife 420 translates along the guide track 422. In contrast, where an extension or torsion spring is employed to place a bias on the knife 420, the increasing force required to extend the knife 420 may diminish the knife output of the blade in the fully extended (distal-most) position. Additionally, the bias on the knife 420 provided by the constant-force or constant torque springs 714 passively adjusts the position of the knife 420 in a proximal direction during articulation of the end effector 204 (FIGS. 2 and 4A) and opening and closing the jaws 210, 212 (FIGS. 2 and 4A), such that the knife 420 does not perform any inadvertent cutting despite changes in geometry of the guide track 422 caused by the articulation or the opening and closing if the jaws 210, 212.

In the event of a system failure, such as a loss of power, a bailout or in the event the drive input 506*f* is otherwise removed from the tool driver, the constant-force springs 714 will naturally drive rotation of the capstan assembly 602*b* in a second angular direction of arrow $E_0$, opposite the first angular direction $A_0$. The internal stress in the constant-force springs 714 will re-coil the constant-force or constant-torque springs 714 around the spools 710, thus causing the coupler 610 and the drive gear 604*b* to rotate in the second angular direction $E_0$. Rotation of the drive gear 604*b* in the second angular direction $E_0$ causes the driven gear 606*b* and the drive rod 416 to translate in the proximal direction $F_0$, thus allowing the knife 420 (FIG. 4B) to return to an un-exposed ("home") position. The constant-force or constant torque springs 714 may maintain the knife 420 in the un-exposed position allowing for the jaws 210, 212 (FIGS. 2 and 4) to be safely opened, closed, articulated cleaned, maintained and prepared for future surgical operations.

Figure 9A:
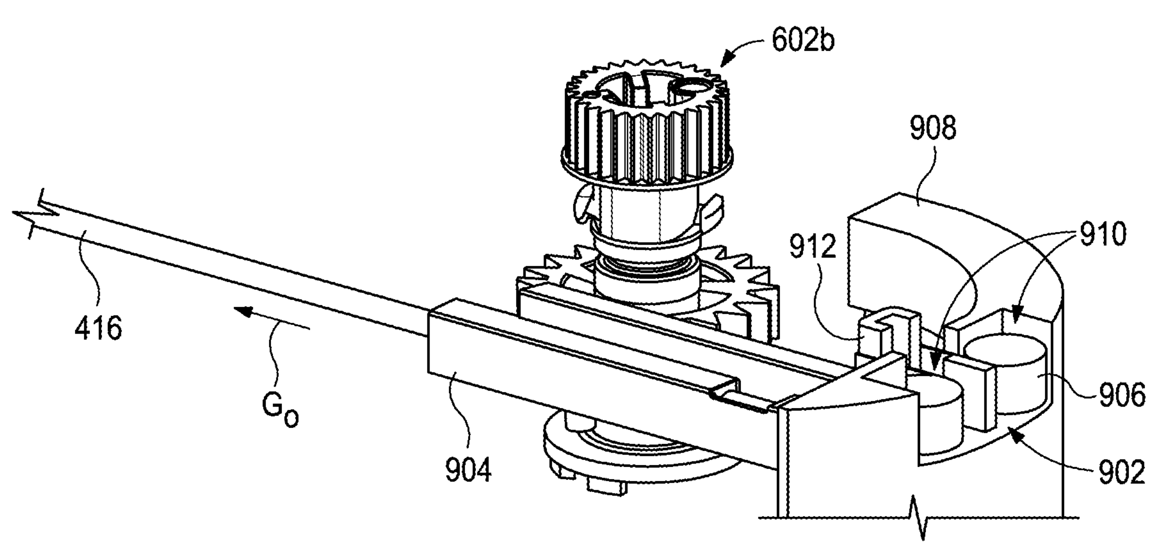
FIGS. 9A and 9B are partial perspective and top views, respectively, of a retraction mechanism coupled to a longitudinally driven gear in a retracted position, according to one or more additional embodiments.
Figure 9B:
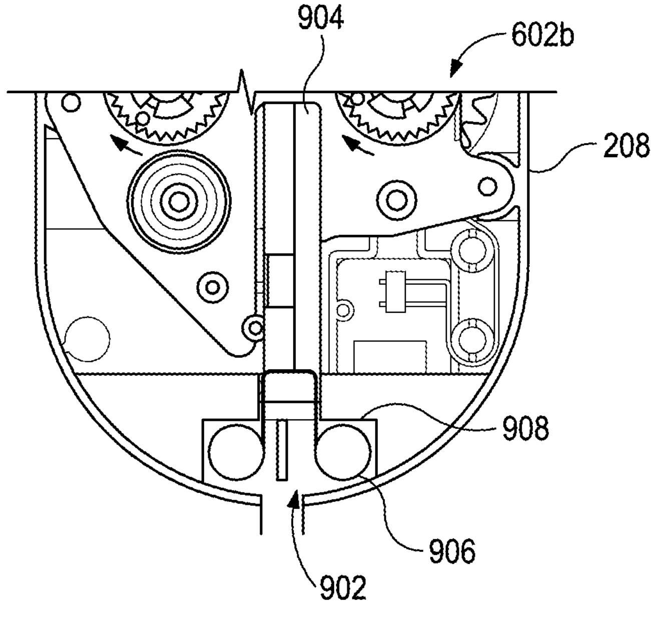
Figure 10A:
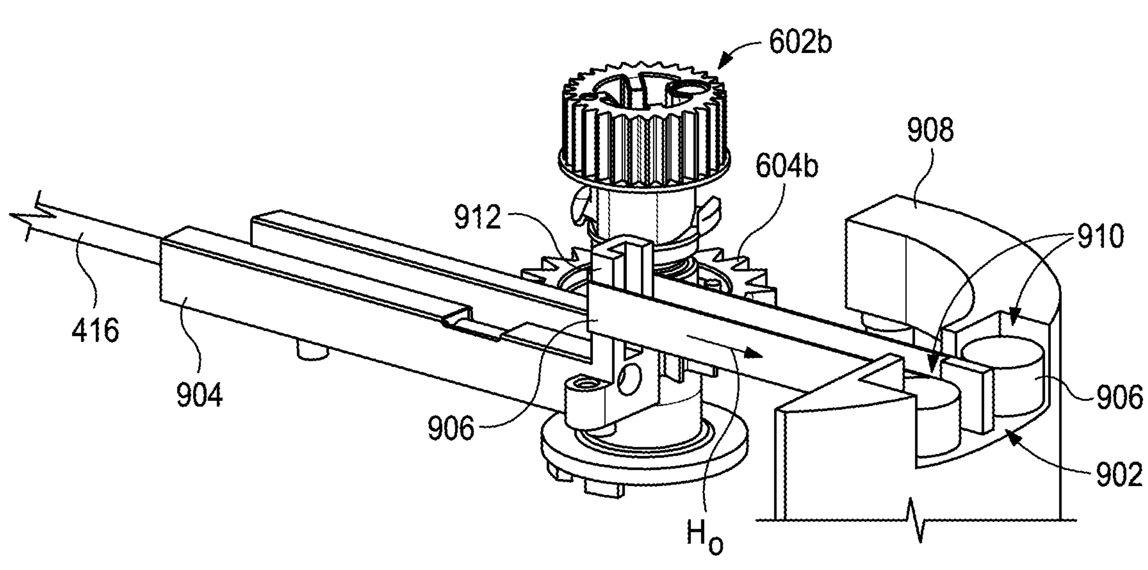
FIGS. 10A and 10B are partial perspective and top views, respectively, of the retraction mechanism of FIGS. 9A and 9B with the longitudinally driven gear in an extended retracted position.
Figure 10B:
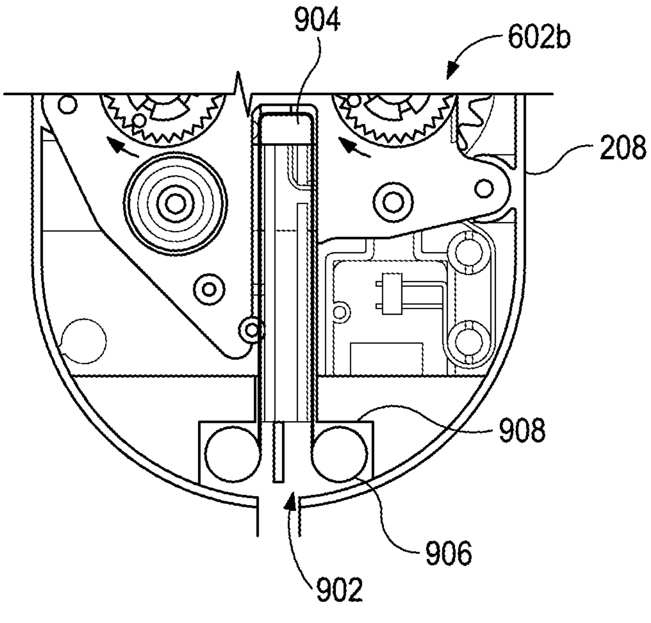

FIGS. 9A and 9B and FIGS. 10A and 10B are partial perspective and top views, respectively, of another example retraction mechanism 902 coupled to a longitudinally driven gear 904, according to one or more additional embodiments. More specifically, FIGS. 9A-9B depict the retraction mechanism 902 urging the longitudinally driven gear 904 to a retracted, "home" or "zero" (proximal) position, and FIGS. 10A-10B depict the longitudinally driven gear 904 moved to an extended or fired (distal) position. It should be appreciated that the "zero" or "home" position of the driven gear 904 illustrated is exemplary, and may not be the exact position of the driven gear 904 required to maintain the knife 420 in the retracted position given the state of the end effector 204 (FIG. 2). As described above, if end effector 202 is in an articulated or unarticulated position, or if the jaws 210, 212 are opened or closed, the driven gear 904 may be moved to a slightly different position.

The longitudinally driven gear 904 may be the same as or similar to the driven gear 606*b* and may thus be operably coupled to the second capstan assembly 602*b*, as generally described above, such that the longitudinally driven gear 904 may be driven in a distal longitudinal direction (arrow $G_0$) by operation of the second capstan assembly 602*b*. The longitudinally driven gear 904 may be coupled to the drive rod 416 such that longitudinal translation of the longitudinally driven gear 904 may operate the knife 420 as described above.

The retraction mechanism 902 includes one or more biasing members, such as a constant-force or constant-torque spring 906, operatively coupled to the longitudinally driven gear 904 and mounted to a chassis member 908. The spring 906 may be constructed as a "twin spring" including two coils in which a first coil is wound clockwise and a second coil is wound counter-clockwise. The spring 906 may thus provide a sufficient force to the drive rod 416 in a confined space. In the illustrated embodiment, the first and second coils of the spring 906 are mounted on lateral sides of the longitudinally driven gear 904 such that the coils cooperate to provide a constant force to the longitudinally driven gear 904 and the drive rod 416. The chassis member 908 may be fixedly coupled to the drive housing 208 in a manner similar to the chassis plate 704 (FIG. 7) described above. In at least one embodiment, the chassis member 908 may form part of the chassis plate 704, but could alternatively form part of the drive housing 208. The constant-force spring 906 may bias the longitudinally driven gear 904 to the retracted (proximal) position, as illustrated in FIG. 9A.

The chassis member 908 includes a pair of cavities 910 defined therein to support the coiled portions of the constant-force spring 906, such as corresponding first and second spools that retain and coil opposing ends of the constant-force spring 906. The constant-force or constant-torque spring 906 extends distally from the cavities the 910 and wraps around a mounting post 912 provided by the longitudinally driven gear 904. In some embodiments, the constant-force or spring 906 may be coupled to the mounting post 912 with threaded fasteners, pins, welds or any attachment mechanisms recognized in the art. In other embodiments, the constant-force spring 906 may simply extend around the mounting post 912 to maintain the constant-force spring 906 in position. This arrangement may simplify an assembly procedure significantly. In still other embodiments, a low spring rate extension or compression spring may be coupled between the chassis member 908 and the mounting post 912 to provide a substantially constant force to the drive rod 416, at least over the operating range of the drive rod 416. In operation, the second capstan assembly **602*b* may be operated to move the longitudinally driven gear 904, the drive rod 416 and the knife 420 (FIG. 4B) in the distal direction $G_0$ to the extended or fired (distal) position, as illustrated in FIGS. 10A and 10B. The distal movement of the longitudinally driven gear 904 causes the constant-force spring 906 to partially uncoil (unwind) from within the cavities 910 (or corresponding spools arranged in the cavities 910), and extend distally as mounted to the longitudinally driven gear 904. The constant-force spring 906 maintains a biasing force on the longitudinally driven gear 904 in a proximal direction (arrow $H_0$). Backlash in the interface between the longitudinally driven gear 904 and the drive gear 604*b*, backlash in the interface between the drive gear 604*b* and the drive input 506*f* and backlash between the drive input 506*f* and the tool driver is eliminated by the biasing force since teeth on the drive gear 604*b* engage only a proximally-facing flank of teeth on the longitudinally driven gear 904. The biasing force also passively adjusts the position of the knife 420 as the end effector 204 (FIGS. 2 and 4) is operated to open and close the jaws 210, 212 or to be articulated in operation, and also returns the knife 420 to the retracted position (FIGS. 9A and 9**B) in the event of a bailout or system failure as described above.

In other embodiments, the single constant-force spring 902 may be replaced with a pair of constant-force springs each having an end coupled to the mounting post 912 and a coiled portion arranged within a corresponding one of the cavities 910. In still other embodiments, instead of wrapping around the mounting post 912, it is contemplated herein to include only a single constant-force spring 902 extending between the longitudinally driven gear 904 and the chassis member 908. In other embodiments, an intermediate member (not shown) may be interposed between the constant-force spring 906 and the longitudinally driven gear 904, without departing from the scope of the disclosure. Coupling the biasing member (constant-force spring 906), directly or indirectly, to the longitudinally driven gear 904 and to provide a proximal bias to the longitudinally driven gear 904 may improve accuracy, e.g., by eliminating backlash, efficiency, e.g., by preventing losses between the drive gear **604*b* and the longitudinally driven gear 904 and safety, e.g., by returning the knife 420** to a safe retracted position when removed from the tool driver.

Figure 11:
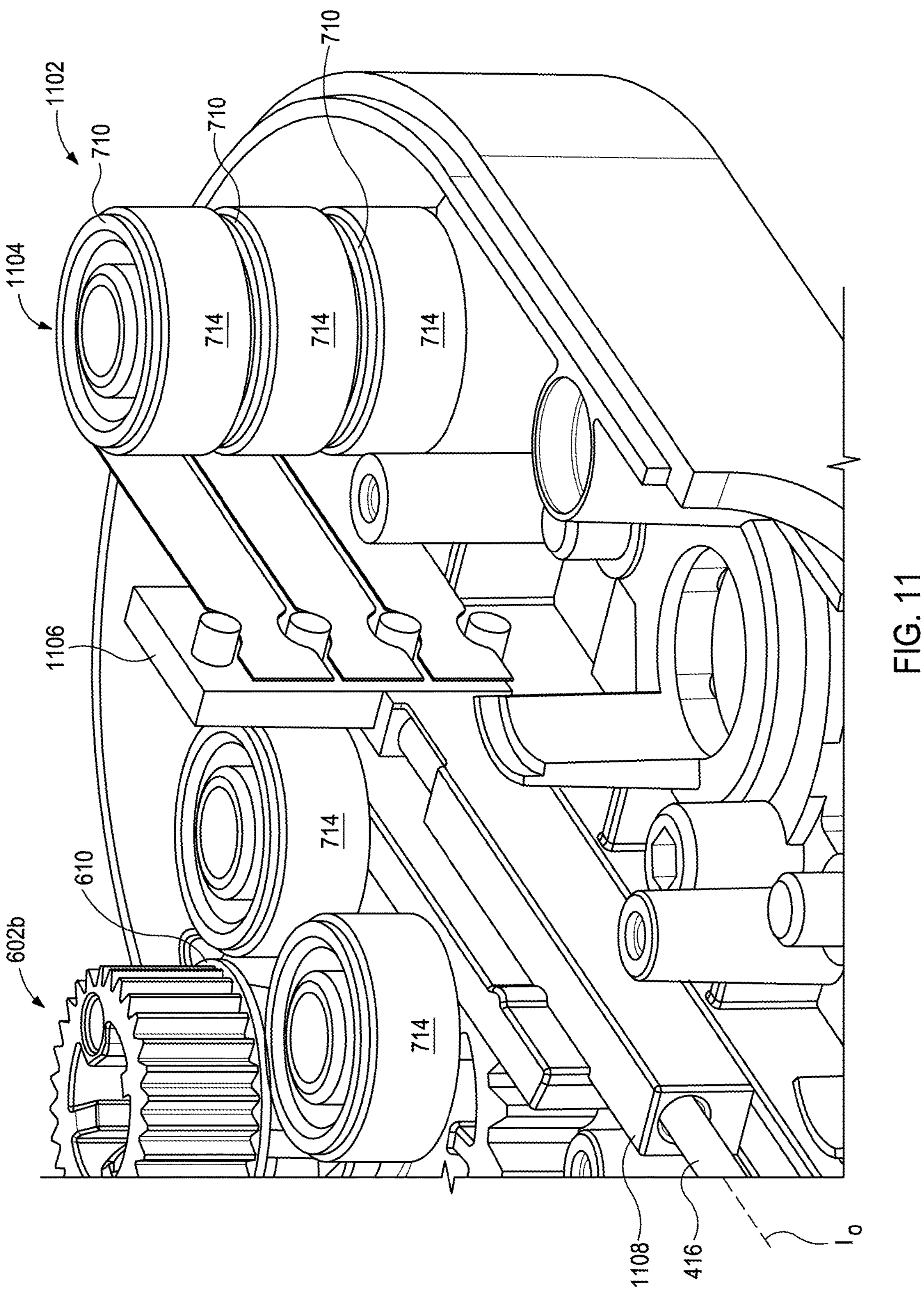
FIG. 11 is a partial, perspective view of a retraction mechanism including a stack of springs, according to one or more additional embodiments.

FIG. 11 is a partial, perspective view of another example retraction mechanism 1102 including a stack 1104 of biasing members, such as constant-force springs 714, according to one or more additional embodiments. As illustrated in FIG. 11, the stack 1104 includes three constant-force springs 714 that can be accommodated within the drive housing 208. More or fewer constant-force springs 714, or other biasing members, may be provided in the stack in other embodiments. This arrangement provides flexibility to add or remove constant-force springs 714 depending the particular biasing force desired or appropriate for a surgical operation.

Each of the constant-force springs 714 is wound around a corresponding spool 710, and has an end fixedly attached to a mounting plate 1106. The mounting plate 1106 is coupled to a longitudinally driven gear 1108 such that the mounting plate 1106 translates longitudinally along with the longitudinally driven gear 1108. In some embodiments, the mounting plate 1106 may be formed monolithically with the longitudinally driven gear 1108. The second capstan assembly **602*b* may be operated to drive the longitudinally driven gear 1108, the drive rod 416 and the mounting plate 1106 together in the direction of arrow $I_0$, as generally described above. As the mounting plate 1106 is moved longitudinally $I_0$, the constant-force springs 714 in the stack 1104 will be caused to wind and unwind from the respective spools 710 while maintaining a bias on the longitudinally driven gear 1108 in a proximal direction. Since the mounting plate 1106 translates longitudinally with the longitudinally driven gear 1108, the constant-force springs 714 coupled to the mounting plate 1106 will eliminate any backlash in the interface between the longitudinally driven gear 1108 and the drive gear 604*b* of the second capstan assembly 602*b*, backlash in the interface between the drive gear 604*b* and the drive input 506*f* as well as backlash between the drive input 506*f* and the tool driver as described above. In other embodiments, the constant-force springs 714 in the stack 1104 may be coupled directly to the longitudinally driven gear 1108**.

As illustrated in FIG. 11, where an additional biasing force is desired, an additional pair of constant-force springs 714 may be attached to the connector 610 of the second capstan assembly **602*b*. The constant-force springs 714 coupled to the coupler 610 will be caused to wind and unwind from the coupler 610 as the second capstan assembly 602*b* is rotated and provide a proximal bias to the knife 420 (FIG. 4B) as described above. In other embodiments, the constant-force springs 714 attached to the coupler 610 may be eliminated from the retraction mechanism 1102**.

Embodiments disclosed herein include:

A. A surgical tool that includes a drive housing, a drive input rotatably mounted to a bottom of the drive housing, a capstan assembly arranged within the drive housing and including a drive gear operatively coupled to the drive input such that rotation of the drive input correspondingly actuates the drive gear, a longitudinally driven gear arranged within the drive housing and engageable with the drive gear such that the longitudinally driven gear translates between a proximal home position and a distal extended position in response to actuation of the drive gear, a drive rod coupled to the longitudinally driven gear and extending from the drive housing to an end effector of the surgical instrument, and at least one biasing member mounted to the drive housing and operatively coupled to at least one of the capstan assembly and the longitudinally driven gear to bias the longitudinally driven gear toward the proximal position with a constant force.

B. A method of operating a surgical tool that includes positioning the surgical tool adjacent a patient, the surgical tool including: a drive housing; a drive input rotatably mounted to a bottom of the drive housing; a capstan assembly arranged within the drive housing and including a drive gear operatively coupled to the drive input; and a longitudinally driven gear arranged within the drive housing and engageable with the drive gear to translate in response to actuation of the drive gear. The method further includes biasing the longitudinally driven member toward a proximal position within the drive housing with a biasing member coupled to at least one of the capstan assembly and the longitudinally driven gear, rotating the drive input to actuate the capstan assembly and thereby translating the longitudinally driven gear in a distal direction, and resisting distal movement of the longitudinally driven gear with a constant force provided by the biasing member.

C. A surgical tool system that includes a drive housing having a drive input rotatably mounted to a bottom thereof, a shaft extending distally from the drive housing and terminating at an end effector, a tool driver operably coupled to the drive housing to selectively rotate the drive input, a capstan assembly arranged within the drive housing and including a drive gear operatively coupled to the drive input such that rotation of the drive input correspondingly actuates the drive gear, a longitudinally driven gear arranged within the drive housing and engageable with the drive gear such that the longitudinally driven gear translates between a proximal home position and a distal extended position in response to actuation of the drive gear, a drive rod coupled to the longitudinally driven gear and extending through the shaft to extend a knife along a guide track defined in the end effector in response to the translation of the longitudinally driven gear toward the distal extended position, and at least one constant force spring mounted to the drive housing and extending to at least one of the capstan assembly and the longitudinally driven gear, wherein the at least one constant force spring constantly biases the longitudinally driven gear toward the proximal position.

Each of the embodiments A, B and C may have one or more of the following additional elements in any combination: Element 1: wherein the at least one biasing member comprises a constant-force spring constructed from band of spring material and defining a coil supported within the drive housing. Element 2: wherein the flat band is operatively coupled to the longitudinally driven gear and translates with the longitudinally driven gear to wind and unwind the band from the coil. Element 3: wherein the band is wrapped around a mounting post defined on the longitudinally driven gear. Element 4: further comprising a mounting plate carried by the longitudinally driven gear, wherein the band is coupled to the mounting plate. Element 5: wherein the band is operatively coupled to the capstan assembly and winds and unwinds from the capstan assembly to coil and uncoil the band from the coil. Element 6: wherein the capstan assembly includes a coupler that includes a hook for securing the band to the coupler. Element 7: further comprising a spool coupled within the drive housing in a fixed location, and wherein the coil is supported around the spool. Element 8: further comprising a mounting plate carried by the longitudinally driven gear, wherein the at least one biasing member includes a stack of biasing members coupled to the mounting plate, and wherein the constant-force spring is included in the stack.

Element 9: wherein rotating the drive input includes rotating the drive input with a tool driver removably coupled to the surgical tool. Element 10: further comprising: decoupling the surgical tool from the tool driver; and urging the longitudinally driven gear toward the proximal position with the biasing member. Element 11: further comprising cleaning the surgical tool while maintaining the longitudinally driven gear in the proximal position with the biasing member. Element 12: further comprising uncoiling the biasing member by drawing a band of the biasing member from a coil of the biasing member supported within the drive housing. Element 13: wherein drawing the band of the biasing member includes distally translating an end of the biasing member coupled to the longitudinally driven gear. Element 14: wherein drawing the band of the biasing member includes winding the band around the capstan assembly as the capstan assembly is actuated. Element 15: further comprising advancing a knife within an end effector of the surgical tool by the translating of the longitudinally driven gear in a distal direction. Element 16: further comprising operating jaws of the end effector, and passively adjusting a position of the knife within the end effector with the biasing member. Element 17: further comprising articulating the end effector, and passively adjusting a position of the knife with the biasing member.

Element 18: wherein the at least one constant force spring is operable to move the longitudinally driven gear to the proximal position in response to decoupling the drive housing from the tool driver.

By way of non-limiting example, exemplary combinations applicable to A, B and C include: Element 2 with Element 1; Element 3 with Element 2; Element 4 with Element 2; Element 5 with Element 1; Element 6 with Element 5; Element 7 with Element 1; Element 10 with Element 9; Element 11 with Element 10; Element 13 with Element 12; Element 14 with Element 12, Element 16 with Element 15 and Element 17 with Element 15.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:

a drive housing;

a drive input rotatably mounted to a bottom of the drive housing;

a capstan assembly arranged within the drive housing and including a drive gear operatively coupled to the drive input such that rotation of the drive input correspondingly actuates the drive gear;

a longitudinally driven gear arranged within the drive housing and engageable with the drive gear such that the longitudinally driven gear translates between a proximal home position and a distal extended position in response to actuation of the drive gear;

a drive rod coupled to the longitudinally driven gear and extending from the drive housing to an end effector of the surgical tool; and at least one biasing member mounted to the drive housing and operatively coupled to at least one of the capstan assembly or the longitudinally driven gear to bias the longitudinally driven gear toward the proximal home position with a constant force, wherein:

the at least one biasing member comprises a constant-force spring constructed from a band of spring material and defining a coil supported within the drive housing;

the band is operatively coupled to the longitudinally driven gear such that translation of the longitudinally driven gear toward the distal extended position unwinds the band from the coil; and the band is wrapped around a mounting post defined on the longitudinally driven gear.

2. The surgical tool of claim 1, further comprising a spool coupled within the drive housing in a fixed location, and wherein the coil is supported around the spool.

3. A surgical tool, comprising:

a drive housing;

a drive input rotatably mounted to a bottom of the drive housing;

a capstan assembly arranged within the drive housing and including a drive gear operatively coupled to the drive input such that rotation of the drive input correspondingly actuates the drive gear;

a longitudinally driven gear arranged within the drive housing and engageable with the drive gear such that the longitudinally driven gear translates between a proximal home position and a distal extended position in response to actuation of the drive gear;

a drive rod coupled to the longitudinally driven gear and extending from the drive housing to an end effector of the surgical tool; and at least one biasing member mounted to the drive housing and operatively coupled to at least one of the capstan assembly or the longitudinally driven gear to bias the longitudinally driven gear toward the proximal home position with a constant force, wherein:

the at least one biasing member comprises a constant-force spring constructed from a band of spring material and defining a coil supported within the drive housing, and the band is operatively coupled to the longitudinally driven gear such that translation of the longitudinally driven gear toward the distal extended position unwinds the band from the coil; and further comprising a mounting plate carried by the longitudinally driven gear and the band is coupled to the mounting plate.

4. The surgical tool of claim 3, wherein the at least one biasing member includes a stack of biasing members coupled to the mounting plate, and wherein the constant-force spring is included in the stack.

5. The surgical tool of claim 3, further comprising a spool coupled within the drive housing in a fixed location, and wherein the coil is supported around the spool.

6. A surgical tool, comprising:

a drive housing;

a drive input rotatably mounted to a bottom of the drive housing;

a capstan assembly arranged within the drive housing and including a drive gear operatively coupled to the drive input such that rotation of the drive input correspondingly actuates the drive gear;

a longitudinally driven gear arranged within the drive housing and engageable with the drive gear such that the longitudinally driven gear translates between a proximal home position and a distal extended position in response to actuation of the drive gear;

a drive rod coupled to the longitudinally driven gear and extending from the drive housing to an end effector of the surgical tool; and at least one biasing member mounted to the drive housing and operatively coupled to at least one of the capstan assembly or the longitudinally driven gear to bias the longitudinally driven gear toward the proximal position with a constant force, wherein:

the band is operatively coupled to the capstan assembly and winds and unwinds from the capstan assembly to coil and uncoil the band from the coil; and the capstan assembly includes a coupler that includes a hook for securing the band to the coupler.

7. The surgical tool of claim 6, further comprising a spool coupled within the drive housing in a fixed location, and wherein the coil is supported around the spool.

8. A surgical tool system, comprising:

a drive housing having a drive input rotatably mounted to a bottom thereof and operably couplable to a tool driver;

a shaft extending distally from the drive housing and terminating at an end effector;

a capstan assembly arranged within the drive housing and including a drive gear operatively coupled to the drive input such that rotation of the drive input correspondingly actuates the drive gear;

a longitudinally driven gear arranged within the drive housing and engageable with the drive gear such that the longitudinally driven gear translates between a proximal home position and a distal extended position in response to actuation of the drive gear;

a drive rod coupled to the longitudinally driven gear and extending through the shaft to a knife; and at least one constant force spring mounted to the drive housing and extending to at least one of the capstan assembly or the longitudinally driven gear, wherein the at least one constant force spring constantly biases the longitudinally driven gear toward the proximal home position, and wherein the at least one constant force spring is operable to move the longitudinally driven gear to the proximal position in response to decoupling the drive housing from the tool driver.

9. The surgical tool of claim 8, wherein the at least one constant-force spring constructed from band of spring material and defining a coil supported within the drive housing.

10. The surgical tool of claim 9, wherein the band is operatively coupled to the longitudinally driven gear and translates with the longitudinally driven gear to wind and unwind the band from the coil.

11. The surgical tool of claim 10, wherein the band is wrapped around a mounting post defined on the longitudinally driven gear.

12. The surgical tool of claim 10, further comprising a mounting plate carried by the longitudinally driven gear, wherein the band is coupled to the mounting plate.

13. The surgical tool of claim 9, wherein the band is operatively coupled to the capstan assembly and winds and unwinds from the capstan assembly to coil and uncoil the band from the coil.

14. The surgical tool of claim 13, wherein the capstan assembly includes a coupler that includes a hook for securing the band to the coupler.

15. The surgical tool of claim 9, further comprising a spool coupled within the drive housing in a fixed location, and wherein the coil is supported around the spool.

16. The surgical tool of claim 8, further comprising a mounting plate carried by the longitudinally driven gear, wherein the at least one biasing member includes a stack of biasing members coupled to the mounting plate, and wherein the constant-force spring is included in the stack.

* * * * *